US012247625B2

(12) United States Patent
Tenne et al.

(10) Patent No.: US 12,247,625 B2
(45) Date of Patent: Mar. 11, 2025

(54) ROTATIONAL COUPLING DEVICE AND METHOD

(71) Applicant: OLYMPUS CORPORATION, Tokyo (JP)

(72) Inventors: Dirk Tenne, Seattle, WA (US); Madeline C. Graham, Sammamish, WA (US)

(73) Assignee: OLYMPUS CORPORATION, Tokyo (JP)

( * ) Notice: Subject to any disclaimer, the term of this patent is extended or adjusted under 35 U.S.C. 154(b) by 479 days.

(21) Appl. No.: 17/680,589

(22) Filed: Feb. 25, 2022

(65) Prior Publication Data
US 2022/0299055 A1 Sep. 22, 2022

Related U.S. Application Data

(60) Provisional application No. 63/155,350, filed on Mar. 2, 2021.

(51) Int. Cl.
*F16D 1/027* (2006.01)
*F16B 11/00* (2006.01)
(Continued)

(52) U.S. Cl.
CPC ............ *F16D 1/027* (2013.01); *F16B 11/008* (2013.01); *F16C 3/023* (2013.01); *A61B 17/32053* (2013.01); *Y10T 403/473* (2015.01)

(58) Field of Classification Search
CPC .... A61B 17/32053; F16B 7/00; F16B 11/008; F16C 3/023; F16D 1/027; F16D 1/068;
(Continued)

(56) References Cited

U.S. PATENT DOCUMENTS 1,941,289 A * 12/1933 Asline .................... E21B 17/04
403/268
2,692,205 A * 10/1954 Greider .................. C04B 35/52
403/265
(Continued)

FOREIGN PATENT DOCUMENTS

JP 2005003087 A 1/2005
WO 2022187219 9/2022

OTHER PUBLICATIONS

"International Application Serial No. PCT/US2022/018303, International Search Report mailed Jun. 9, 2022", 5 pgs.
(Continued)

*Primary Examiner* — Josh Skroupa
(74) *Attorney, Agent, or Firm* — Schwegman Lundberg & Woessner, P.A.

(57) ABSTRACT

In an illustrative embodiment, an apparatus includes a first rod formed from a first material and a second rod formed from a second material. The first rod includes a first end defining a cavity exposed at an end of the first rod. The cavity has a cavity length and a cavity width perpendicular to a longitudinal axis of the first rod. The cavity length is greater than the cavity width. The second rod includes a first section and a second section. The first section has a width that corresponds to the cavity width and a length that corresponds to the cavity length. The apparatus includes a bonding structure that attaches the first rod to the second rod.

17 Claims, 5 Drawing Sheets

(51) Int. Cl.
*F16C 3/02* (2006.01)
*A61B 17/3205* (2006.01)

(58) Field of Classification Search
CPC ............ F16D 2001/102; Y10T 403/47; Y10T 403/473; Y10T 403/477; Y10T 403/478; Y10T 403/479; Y10T 403/7098
USPC ................ 403/265, 268, 270, 271, 272, 383
See application file for complete search history.

(56) References Cited

U.S. PATENT DOCUMENTS

| | | | | |
|---|---|---|---|---|
| 4,722,630 | A * | 2/1988 | Fang | F01D 5/025 403/272 |
| 4,991,991 | A * | 2/1991 | Ito | F16D 1/064 403/272 |
| 5,980,471 | A * | 11/1999 | Jafari | F16C 1/02 600/585 |
| 7,188,456 | B2 * | 3/2007 | Knauseder | E04F 15/02 403/268 |
| 2004/0039310 | A1 | 2/2004 | Burkett | |
| 2008/0056813 | A1 | 3/2008 | Viernekes | |
| 2019/0120283 | A1* | 4/2019 | Faulkner | F16C 3/023 |

OTHER PUBLICATIONS

"International Application Serial No. PCT/US2022/018303, Written Opinion mailed Jun. 9, 2022", 6 pgs.
"International Application Serial No. PCT US2022 018303, International Preliminary Report on Patentability mailed Sep. 14, 2023", 8 pgs.

\* cited by examiner

ROTATIONAL COUPLING DEVICE AND METHOD

PRIORITY CLAIM

This application claims the benefits of U.S. Provisional Application No. 63/155,350 filed Mar. 2, 2021, the contents of which are hereby incorporated by reference.

BACKGROUND

The statements in this section merely provide background information related to the present disclosure and may not constitute prior art.

Certain medical devices, such as needles, cytology brushes, coring tools, or the like, may be composed of dissimilar medical-grade metals. Welding dissimilar metals, such as nitinol and stainless steel, tends to be extremely difficult due to the formation of intermetallics in the weld zone, which results in joints that are susceptible to sheer forces. There are medical grade adhesives that can create fairly strong bonds between dissimilar metals. However, these bonds are suboptimal for components that will undergo rotational motion that may result in sheering forces that can overwhelm the adhesives.

As an alternative, dissimilar metals can be joined by way of such mechanical processes as crimping, swaging, bonding, or heat shrinking. However, these processes may result in joints that have less strength than welds.

BRIEF SUMMARY

Various disclosed embodiments include illustrative apparatuses, medical systems, and methods for attaching two dissimilar materials.

In an illustrative embodiment, an apparatus includes a first rod formed from a first material and a second rod formed from a second material. The first rod includes a first end defining a cavity exposed at an end of the first rod. The cavity has a cavity length and a cavity width perpendicular to a longitudinal axis of the first rod. The cavity length is greater than the cavity width. The second rod includes a first section and a second section. The first section has a width that corresponds to the cavity width and a length that corresponds to the cavity length. The apparatus includes a bonding structure that attaches the first rod to the second rod.

In another illustrative embodiment, a medical system includes a handle; a first rod couplable to the handle, a second rod formed from a second material, and a bonding structure. The first end of the first rod defines a cavity exposed at an end of the first rod. The cavity has a cavity length and a cavity width perpendicular to a longitudinal axis of the first rod. The cavity length is greater than the cavity width. The second rod includes a first section and a second section. The first section has a width that corresponds to the cavity width and a length that corresponds to the cavity length. The bonding structure attaches the first rod to the second rod.

In another illustrative embodiment, a method includes forming a cavity into an end of a first rod, forming an end of a second rod to fit within the cavity of the first rod, inserting the formed end of the second rod into the first rod, and securing the second rod to the first rod. The cavity and the formed end of the second rod allow torque transmission between the first rod in the second rod.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Illustrative embodiments are illustrated in referenced figures of the drawings. It is intended that the embodiments and figures disclosed herein are to be considered illustrative rather than restrictive.

Like reference symbols in the various drawings generally indicate like elements.

DETAILED DESCRIPTION

Figure 1:
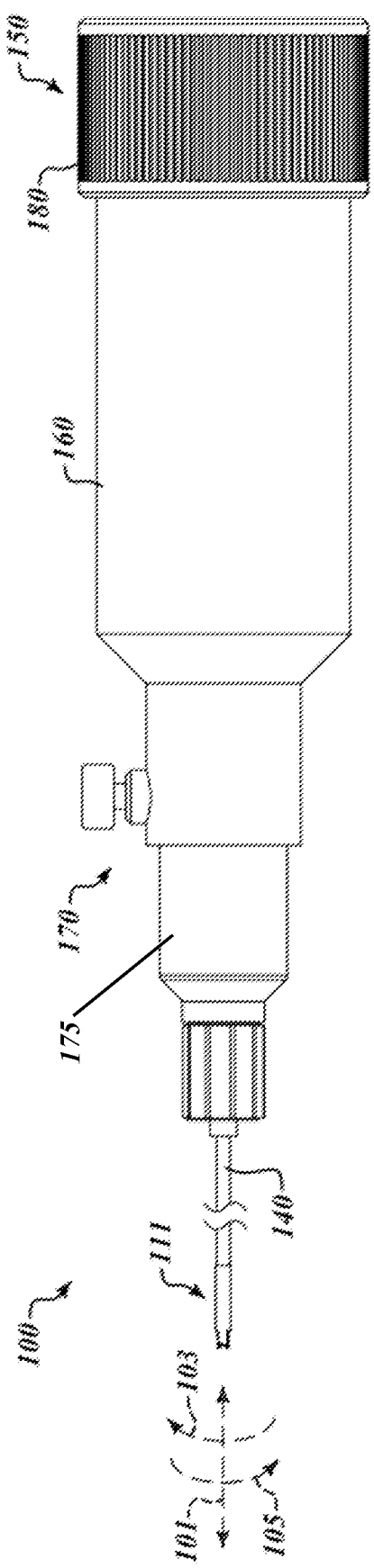
FIG. 1 is a side view of a medical tool.
Figure 2:
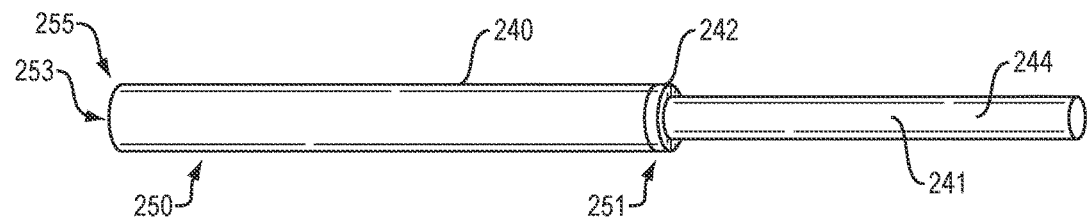
FIG. 2 is a partial side view of a first metal rod coupled to a second metal rod.
Figure 3:
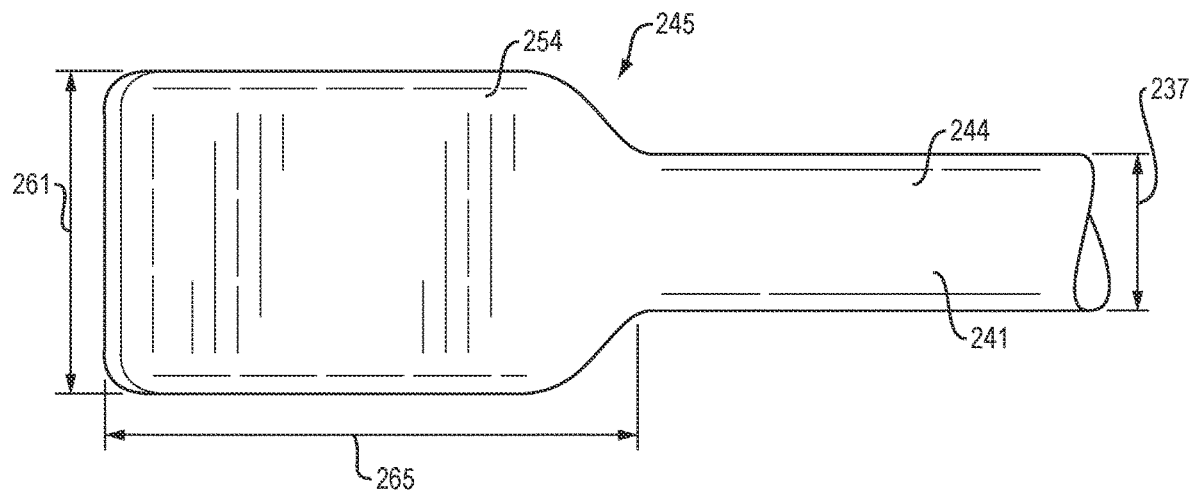
FIG. 3 is a partial first side view of the second metal rod of FIG. 2.
Figure 4:
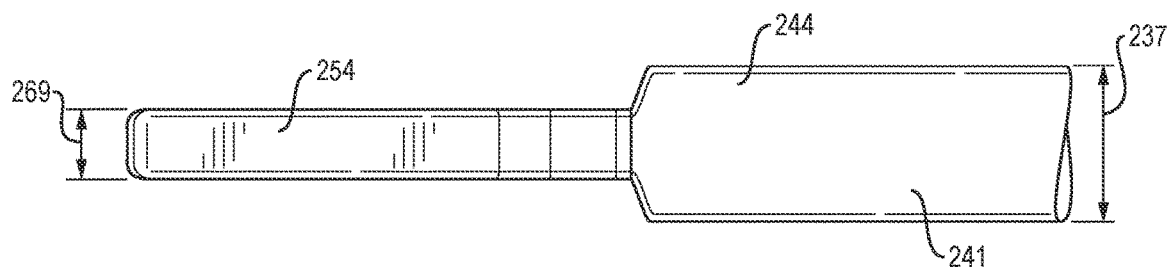
FIG. 4 is a partial second side view of the second metal rod of FIG. 2.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Various disclosed embodiments include illustrative apparatuses, medical systems, and methods for translating rotational forces between rods of dissimilar materials.

Referring now to FIG. 1 and given by way of overview, in various embodiments, an illustrative system 100 is provided for cutting an opening in a tissue wall in an anatomical region of a patient (not shown in FIG. 1). In various embodiments, the system 100, in general, includes a cutting apparatus 111, a control apparatus 150 for controlling the cutting apparatus 111, and a drive shaft assembly 140 coupling the cutting apparatus 111 with the control apparatus 150 to transfer rotational force from the control apparatus 150 to the cutting apparatus 111. As will be described in detail below, the cutting apparatus 111 is a counter-rotatable cutting apparatus having cutting members configured to rotate in directions 103 or 105 about an axis 101. In various embodiments, the drive shaft assembly 140 includes a first drive shaft and a second drive shaft (not shown in FIG. 1) which, in some embodiments, includes a hollow shaft coaxially disposed around the first drive shaft. The first drive shaft and the second drive shaft are couplable with members of the cutting apparatus 111 and contained in a sheath. In some embodiments, the first drive shaft and the second drive shaft include flexible, counter-rotatable cables. The control apparatus 150 includes a housing 160 that supports a position adjustment apparatus 170 and at least one rotation grip 180. The drive shaft 140 is coupled to the housing 160. A shaft handle portion 175 is connected to a sheath that covers the drive shaft assembly 140. The shaft handle portion 175 is slidably received within the position adjustment apparatus 170. The position adjustment apparatus 170 enables the housing 160 that is connected to the drive shaft assembly 140 to be moved relative to the shaft 175.

Referring additionally to FIGS. 2-6, in various embodiments the drive shaft assembly 140 and/or the cutting apparatus 111 includes a first rod 240 and a second rod 244. The first rod 240 may be formed of a first material, such as stainless steel, and the second rod 244 may be formed of a second material, such as nitinol, connected to a second rod 240, which may be formed of a second material. In various embodiments, a first section 245 of the second rod 244 includes a flattened end that may be shaped into the form of a paddle 254 that is configured to fit into a cavity 250. The cavity 250 exposed at a first end 251 of the first rod 240, and the cavity 250 may be etched, machined, or molded into a first end 251 of the first rod 240. In various embodiments, the cavity 250 extends to an opening 253 formed in an end face 255 of the first rod 240. The first, flattened section of the second rod 244 is received within the cavity 250 of the first rod 240.

Figure 5:
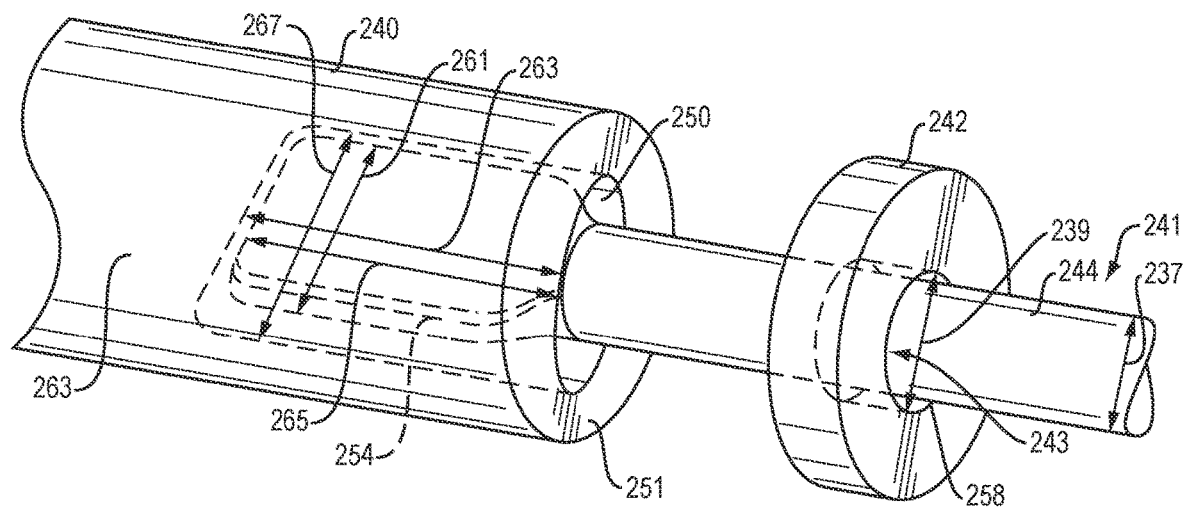
FIG. 5 is a partial perspective, hidden line view of the second metal rod received within the first metal rod prior to attaching two rods together.
Figure 6:
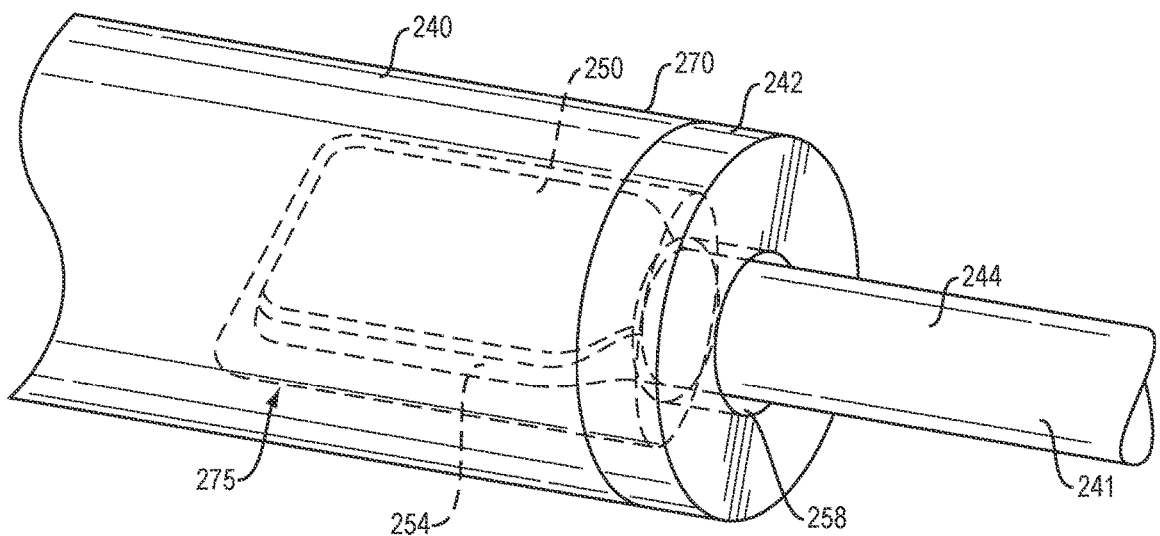
FIG. 6 is a partial perspective, hidden line view of the second metal rod received within the first metal rod after the two rods have been attached together.

A cap 242 is slidably moved over the second rod 244 from a non-flattened end 241 until the cap 242 contacts the first end 251 of the first rod 240 (FIG. 5). The cap 242 includes an opening 243, such as a hole or slot, with a hole width 239 that allows a second section 241 of the second rod 244 to pass therethrough. In various embodiments, the second section 241 of the second rod 244 includes a non-flattened section. The cap 242, such as a collar, disc, horseshoe, or the like, has the same or similar material properties as the second rod 240.

In various embodiments, the paddle 254 of the first section 245 of the second rod 244 has a width 261 that is wider than the hole width 239 of the opening 243 of the cap 242 and approximately equal to a cavity width 267 of the cavity 250. In various embodiments, a cavity length 263 of the cavity 250 in the second rod 240 is slightly greater than a first length 265 of the paddle 254. At a joint 270 between the first rod 240 and the cap 242, the cap 242 is joined to the first rod 240 with a bonding structure, such as a weld or an adhesive, thus securing the paddle 254 within the cavity 250 and, thus, securing the second rod 244 to the first rod 240 with the cap 242. When the second rod 244 is rotated, the paddle 254 engages the interior walls 275 of the cavity 250, causing the first rod 240 to also rotate.

The first width 261 of the paddle 254 (FIG. 3) of the second rod 244 is greater than a diameter 237 of the non-flattened end 241 of the first rod 244 that is proximal of the paddle 254. Also, the paddle 254 has a thickness 269 (FIG. 4) that is less than the diameter of the non-flattened section of the first rod 244.

The shape of the paddle 254 may be attained a number of different ways. For example, the first rod 244 may be flattened mechanically, thermally, or the like. It will be appreciated that the paddle 254 and the cavity 250 may each include any matching configuration such that, when the first rod 244 is engaged with the second rod 240 as previously described, rotational force applied to the first rod 244 is transmitted to the second rod 240. Also, the rods 240 and 244 may have various cross-sectional configurations, such as round, square, rectangular, or the like.

In various embodiments, the paddle 254 and the non-flattened part of the second rod 244 may be separately created components. After the paddle 254 and the non-flattened end 241 of the second rod 244 have been formed, the paddle 254 and the non-flattened end 241 may be bonded together with a weld, adhesive, or the like.

After the paddle 254 of the second rod 244 has been received within the cavity 250 and the cap 242 has been received over the second rod 244 to join it to the first end 251 of the first rod 240, the cap 242 is then welded to the first rod 240 or adhered to the first rod 240 using an adhesive.

Figure 7:
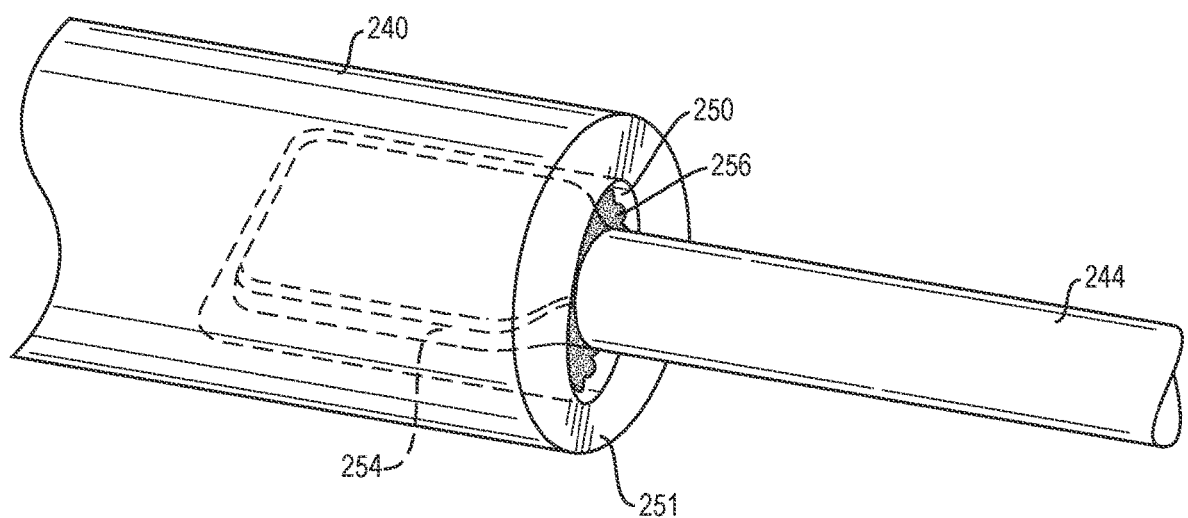
FIG. 7 is a partial perspective, hidden line view of the second metal rod received within the first metal rod in a second configuration.

Referring additionally to FIG. 7, in various embodiments, the second rod 244 is secured within the cavity 250 of the first rod 240 without using the cap 242. In various embodiments, the paddle 254 of the second rod 244 is inserted into the cavity 250 of the first rod 240. In one embodiment, the paddle 254 is welded within the cavity 250 of the first rod 240. In another embodiment, a medical grade adhesive 256 is inserted into the cavity 250 with the paddle 254, thus securing the second rod 244 to the first rod 240. The weld/adhesive allows for axial fixation and still allows transmission of torque or other rotational force between the first rod 244 and the second rod 240.

Figure 8:
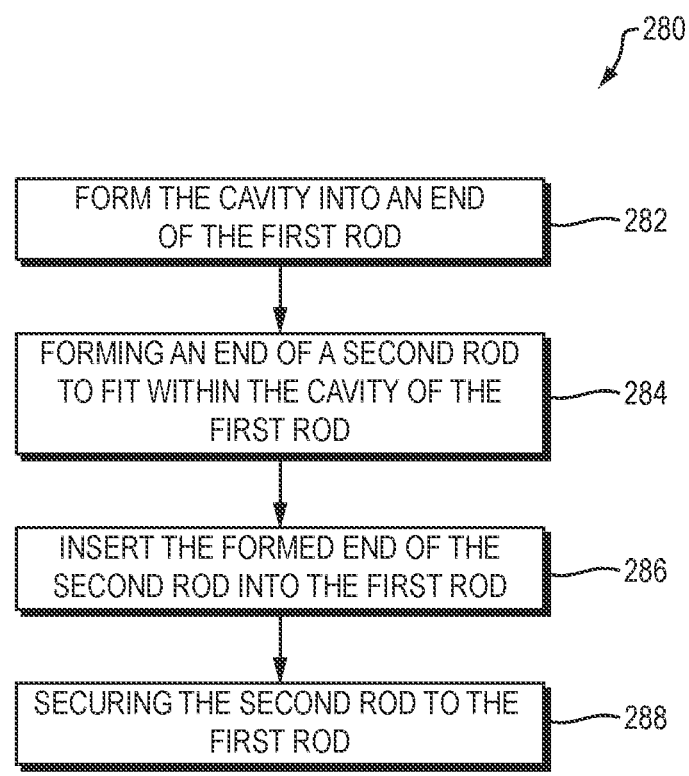
FIG. 8 is a flow chart of an illustrative method for making the tool of FIG. 1.

Referring additionally to FIG. 8, in various embodiments an illustrative method 280 is performed for creating a medical device. At a block 282, the cavity 250 is formed into an end of the first rod 240. At a block 284, the paddle 254 is formed at one end of the second rod 244 in order to fit within the cavity 250 of the first rod 240. At a block 286, the paddle 254 is inserted into the cavity 250, then, at a block 288, the paddle 254 is secured, such as by welding or adhering the cap 242, into the first rod 240. The cavity 250 and the paddle 254 are configured to allow torque transmission between the second rod 244 and the first rod 240.

The proximal end of the first rod 240 is attached to a handle, such as is shown in FIG. 1. Also, a tissue coring feature, such as is shown in FIG. 1, is created at a second end of the second rod 244.

From the foregoing discussion and associated drawing figures, it will be appreciated that various embodiments have been disclosed and illustrated. To that end and without any implication of any limitation (which is not to be inferred), the following paragraphs set forth non-limiting summaries of various embodiments disclosed herein by way of example only and not of limitation:

A. An apparatus comprising: a first rod formed from a first material, the first rod including a first end configured to define a cavity exposed at an end of the first rod, the cavity having a cavity length and a cavity width perpendicular to a longitudinal axis of the first rod, the cavity length being greater than the cavity width; a second rod formed from a second material, the second rod including a first section and a second section, the first section having a width that corresponds to the cavity width and a length that corresponds to the cavity length; and a bonding structure configured to attach the first rod to the second rod.

B. The apparatus of A, wherein the second section of the second rod has a cross-sectional dimension that is less than the width of the first section, and the cross-sectional dimension of the second section of the second rod is greater than a thickness of the first section.

C. The apparatus of A, wherein the bonding structure comprises a weld between the first and second rods at an opening of the cavity.

D. The apparatus of A, wherein the bonding structure includes: a cap having a passageway having a dimension being greater than the cross-sectional dimension of the second rod and less than the first dimension of the first section; and an additional bonding structure configured to bond the collar to a surface of the first rod around the cavity.

E. The apparatus of D, wherein the additional bonding structure includes a weld joint between the first and second rods within the cavity.

F. The apparatus of D, wherein the additional bonding structure includes an adhesive applied between the first and second rods at an opening of the cavity.

G. The apparatus of A, wherein the bonding structure comprises an adhesive applied between the first and second rods within the cavity.

H. The apparatus of A, wherein the first material comprises stainless steel.

I. The apparatus of H, wherein the second material comprises nitinol.

J. A medical system comprising: a handle; a first rod couplable to the handle, the first rod formed from a first material, the first rod configured to define a cavity exposed at an end of the first rod, the cavity having a cavity length and a cavity width perpendicular to a longitudinal axis of the first rod, the cavity length being greater than the cavity width; a second rod formed from a second material, the second rod including a first section and a second section, the first section having a width that corresponds to the cavity width and a length that corresponds to the cavity length; and a bonding structure configured to attach the first rod to the second rod.

K. The medical system of J, wherein the second section of the second rod has a cross-sectional dimension that is less than the width of the first section, and the cross-sectional dimension of the second section of the second rod is greater than a thickness of the first section.

L. The medical system of K, wherein the bonding structure comprises a weld between the first and second rods at an opening of the cavity.

M. The medical system of claim 10, wherein the boding structure includes: a cap having a passageway having a dimension being greater than the cross-sectional dimension of the second rod and less than the first dimension of the first section; and an additional bonding structure configured to bond the collar to a surface of the first rod around the cavity.

N. The medical system of M, wherein the bonding structure includes a weld joint between the first and second rods within the cavity.

O. The medical system of M, wherein the bonding structure includes an adhesive applied between the first and second rods at an opening of the cavity.

P. The medical system of J, wherein the bonding structure includes adhesive applied between the first and second rods within the cavity.

Q. The medical system of J, wherein the first material includes stainless steel.

R. The medical system of Q, wherein the second material includes nitinol.

S. A method comprising: forming a cavity into an end of a first rod; forming an end of a second rod to fit within the cavity of the first rod; inserting the formed end of the second rod into the first rod; and securing the second rod to the first rod, wherein the cavity and the formed end of the second rod are configured to allow torque transmission between the first rod in the second rod.

T. The method of S, wherein securing the second rod to the first rod includes: passing a collar over a second end of the second rod; and bonding the collar to the end of the first rod.

In some instances, one or more components may be referred to herein as "configured to," "configured by," "configurable to," "operable/operative to," "adapted/adaptable," "able to," "conformable/conformed to," etc. Those skilled in the art will recognize that such terms (for example "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While the disclosed subject matter has been described in terms of illustrative embodiments, it will be understood by those skilled in the art that various modifications can be made thereto without departing from the scope of the claimed subject matter as set forth in the claims.

What is claimed is:

1. An apparatus comprising:
    a first rod formed from a first material, the first rod including a first end configured to define a cavity exposed at an end of the first rod, the cavity having a cavity length and a cavity width perpendicular to a longitudinal axis of the first rod, the cavity length being greater than the cavity width;
    a second rod formed from a second material, the second rod including a first section and a second section, the first section having a flattened end in a paddle shape including a paddle width that corresponds to the cavity width, a paddle thickness, and a length that corresponds to the cavity length, the second section having a cross-sectional dimension that is less than the paddle width and greater than the paddle thickness; and
    a bonding structure configured to attach the first rod to the second rod.

2. The apparatus of claim 1, wherein the bonding structure comprises a weld between the first and second rods at an opening of the cavity.

3. The apparatus of claim 1, wherein the bonding structure includes:
    a cap having a passageway having a dimension being greater than the cross-sectional dimension of the second rod and less than the paddle width of the first section; and
    an additional bonding structure configured to bond the cap to a surface of the first rod around the cavity.

4. The apparatus of claim 3, wherein the additional bonding structure includes a weld joint between the first and second rods within the cavity.

5. The apparatus of claim 3, wherein the additional bonding structure includes an adhesive applied between the first and second rods at an opening of the cavity.

6. The apparatus of claim 1, wherein the bonding structure comprises an adhesive applied between the first and second rods within the cavity.

7. The apparatus of claim 1, wherein the first material comprises stainless steel.

8. The apparatus of claim 7, wherein the second material comprises nitinol.

9. A medical system comprising:
    a handle;
    a first rod couplable to the handle, the first rod formed from a first material, the first rod configured to define a cavity exposed at an end of the first rod, the cavity having a cavity length and a cavity width perpendicular to a longitudinal axis of the first rod, the cavity length being greater than the cavity width;
    a second rod formed from a second material, the second rod including a first section and a second section, the first section having a flattened end in a paddle shape including a paddle width that corresponds to the cavity width, a paddle thickness, and a length that corresponds to the cavity length, the second section having a cross-sectional dimension that is less than the paddle width and greater than the paddle thickness; and
    a bonding structure configured to attach the first rod to the second rod.

10. The medical system of claim 9, wherein the bonding structure comprises a weld between the first and second rods at an opening of the cavity.

11. The medical system of claim 9, wherein the bonding structure includes:
    a cap having a passageway having a dimension being greater than the cross-sectional dimension of the second rod and less than the paddle width of the first section; and
    an additional bonding structure configured to bond the cap to a surface of the first rod around the cavity.

12. The medical system of claim 11, wherein the bonding structure includes a weld joint between the first and second rods within the cavity.

13. The medical system of claim 11, wherein the bonding structure includes an adhesive applied between the first and second rods at an opening of the cavity.

14. The medical system of claim 9, wherein the bonding structure includes adhesive applied between the first and second rods within the cavity.

15. The medical system of claim 9, wherein the first material includes stainless steel.

16. The medical system of claim 15, wherein the second material includes nitinol.

17. An apparatus comprising:
    a first rod formed from a first material, the first rod including a first end configured to define an oblong cavity exposed at an end of the first rod;
    a second rod formed from a second material, the second rod including a paddle section and a second section including a circular cross-sectional shape with a first diameter, the paddle section having a width greater than the first diameter, a thickness less than the first diameter, and a length; and
    a bonding structure configured to attach the first rod to the second rod,
    wherein the oblong cavity is dimensioned to receive the paddle section of the second rod and includes at least one dimension perpendicular to a longitudinal axis of the first rod smaller than the first diameter.

* * * * *